United States Patent [19]

Maryanoff et al.

[11] Patent Number: 4,745,185
[45] Date of Patent: May 17, 1988

[54] D-ARABINOSE-1,5-DIPHOSPHATE SALTS AND METHODS FOR THE TREATMENT OF DIABETES

[75] Inventors: Bruce E. Maryanoff, New Hope; Allen B. Reitz, North Wales, both of Pa.

[73] Assignee: McNeilab, Inc., Fort Washington, Pa.

[21] Appl. No.: 808,132

[22] Filed: Dec. 12, 1985

Related U.S. Application Data

[63] Continuation of Ser. No. 614,914, May 29, 1984, abandoned.

[51] Int. Cl.$^4$ .................. A61K 31/665; C07H 11/04; C07H 13/00
[52] U.S. Cl. .................................. 536/117; 514/866; 536/4.1
[58] Field of Search ................. 536/4.1, 117; 514/866, 514/25

[56] References Cited

PUBLICATIONS

S. J. Pilkis, et al., Academic Press, Inc., vol. 89, pp. 101–107 (1982).
G. M. Tener, et al., Journal of the American Chemical Society, vol. 80, pp. 1999–2004 (1958).
Gene F. Tutwiler, Biochemical Medicine, vol. 22, pp. 204–213, Academic Press, Inc. (1979).
Motoyuki Yajima and Michio Ui, American Journal of Physiology, vol. 227, pp. 1–8, (1974), Department of Physiological Chemistry, Faculty of Pharmaceutical Sciences, Hokkaido University.
Pilkis et al., The Journal of Biological Chemistry, vol. 256, No. 7, pp. 3171–3174, (1981), Departments of Physiology and Molecular Biology, Vanderbilt University.
Benkovic et al., Biochemistry, vol. 10, No. 26, pp. 4881–4887, (1971), Department of Chemistry, The Pennsylvania State University.
Benkovic et al., " . . . Fructose-1,6-Diphosphatase Inhibition by Structural Analogs of Fructose 1,6-Diphosphate", Chem. Abs. 76:43379s (1971).
Stryer, Biochemistry (2d Ed.), p. 543 (FIG. 23–8) (1981).

*Primary Examiner*—Ronald W. Griffin
*Attorney, Agent, or Firm*—David J. Levy

[57] ABSTRACT

Novel D-arabinose-1,5-diphosphate salts of the formula (I):

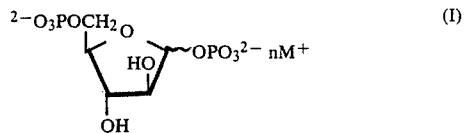

wherein n is from about 3 to 4 and M$^+$ is a cation as well as racemic and isomeric mixtures of the so-defined and forms of formula (I) are useful as hypoglycemic agents for the treatment of diabetes, e.g., in man.

19 Claims, No Drawings

D-ARABINOSE-1,5-DIPHOSPHATE SALTS AND METHODS FOR THE TREATMENT OF DIABETES

This application is a continuation of U.S. Ser. No. 614,914, filed May 29, 1984, now abandoned.

BACKGROUND OF THE INVENTION

Glucose utilization, i.e. glycolysis, and de novo biosynthesis of glucose, i.e. gluconeogenesis, are important metabolic pathways and directly affect the diabetic condition, e.g. in man. The understanding of their biochemical control has been greatly enhanced by the discovery of β-D-fructose-2,6-diphosphate of the following formula (A):

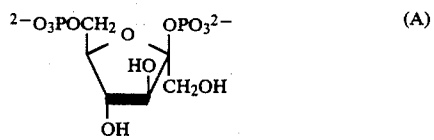

(A)

as a crucial regulating agent, see S. J. Pilkis et al. in The Journal of Biological Chemistry, Vol. 256, No. 7, pp. 3171-3174 (1981). Diphosphate (A) activates glycolysis by stimulating 6-phosphofructo-1-kinase which is the enzyme that converts fructose-6-phosphate into fructose-1,6-diphosphate and also deactivates gluconeogenesis by inhibiting fructose-1,6-biphosphatase, which is the enzyme that catalyzes the reverse reaction.

It is an object of the invention to provide compounds which are related in structure to the compound of formula (A), which possess similar biological activity and which are readily synthesized.

SUMMARY OF THE INVENTION

The individual β and α isomers and isomeric mixtures of D-arabinose-1,5-diphosphate of the following formula (I):

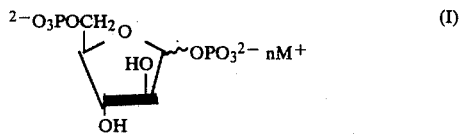

(I)

where n is about 3–4 and M is a cation, are useful in the control of serum glucose levels in an animal and are therefore useful in the treatment of diabetes. Compounds of formula (I) inhibit fructose-1,6-biphosphatase and activate 6-phosphofructo-1-kinase.

DETAILED DESCRIPTION OF THE INVENTION

Compounds of the invention are the α and β isomers of D-arabinose-1,5-diphosphate and are of the following formula (I):

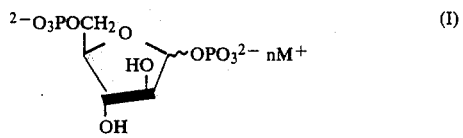

(I)

wherein n is about 3 to 4 and M is a cation. The individual β isomer of formula (I) is of the following formula (II):

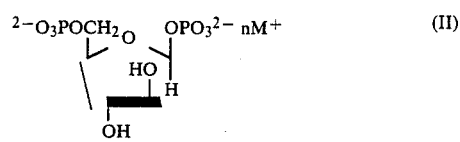

(II)

and the α isomer is of the following formula (III):

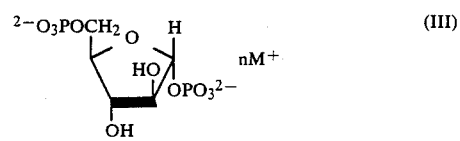

(III)

wherein n and $M^+$ are as defined for formula (I). The present invention encompasses the formula (I) compounds as well as the individual isomers (II) and (III), and isomer mixtures of (II) and (III) e.g., (II):(III) of 80:20.

In the formulae (I), (II) and (III), "n" may be less than the stoichiometric 4 or may be more than 4. In the preparation of the salt, one or more the anionic centers of (I), (II) or (III) may be protonated which would result in the isolated salt needing less than the 4 cations which would be required in the formula as drawn. Thus, the number of M cations may be less than 4, e.g., about 3 to 4. More than the stoichiometric 4 moles of the base M may be seen in the final product in view of entrapment of a small amount of base in the solid product. "$M^+$" in formulae (I), (II) and (III) may be a cation of an organic or inorganic base. Organic bases include primary, secondary and tertiary amines such as ethylamine, diethylamine, triethylamine, or cyclohexylamine and quaternary ammonium compounds such as tetra-n-butylammonium. Inorganic bases include those with cations such as sodium, potassium, lithium and calcium, with examples of bases being sodium bicarbonate, potassium hydroxide and calcium carbonate.

The synthesis of formula (I) salts may proceed from 2,3,5-tri-O-benzyl-D-arabinofuranose which is available from Pfanstiehl of Waukegan, Ill., of the following formula (IV):

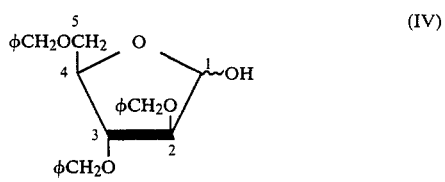

(IV)

Arabinofuranose (IV) is acetylated, e.g., with acetic anhydride to yield the acetate (V) as an α:β mixture of a ratio of about 7:3. Acetate (V) may be taken on to the formula (II) or formula (III) isomer as outlined in the following scheme:

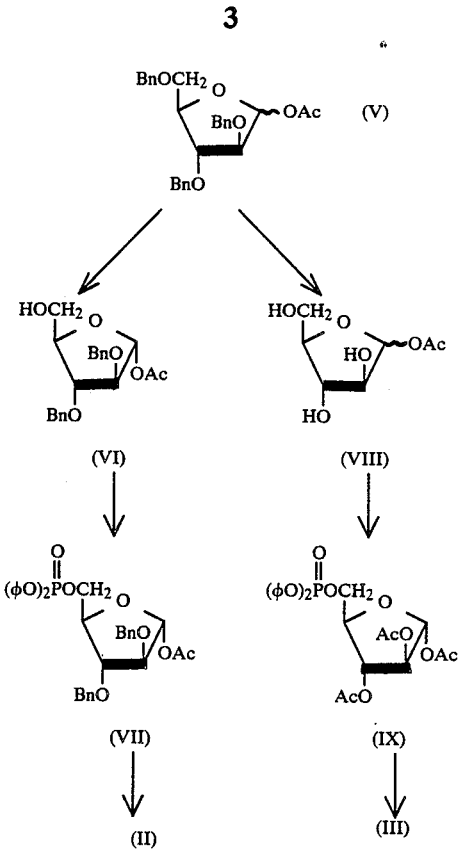

wherein Bn is benzyl, Ac is acetyl and φ is phenyl.

In the scheme leading to formula (II), the acetate (V) is subjected to hydrogenolysis to selectively remove the primary benzyl ether using a pyridine-poisoned palladium catalyst, e.g. with 10% Pd on carbon at 50 psig of H$_2$, 0.4% pyridine:substrate (w:w) in methanol/acetic acid for about 24 hours, to yield alcohol (VI) exclusively as the α anomer. Alcohol (VI) is then phosphorylated to yield phosphate (VII), e.g. by reaction with (φO)$_2$POCl in pyridine. Phosphate (VII) is then subjected to three reactions-in turn, bromination (displacing the OAc moiety), phosphorylation (to displace the bromo atom) with (φCH$_2$O)$_2$PO$_2^-$—(CH$_3$CH$_2$)$_3$NH$^+$, and simultaneous cleavage of the six protecting groups, e.g., with lithium metal in liquid ammonia at −78° C. for one hour to yield formula (II), e.g. as the tetralithium salt. From the tetralithium salt of (II), i.e. formula (II) wherein n is 4 and M$^+$ is Li$^+$, other salts such as the cyclohexylammonium salt may be produced by conventional means. The high stereoselectivity for the β isomer (II) (β:α in the product would be about 92:8) is probably associated with the epimerization of the bromo compound in the (VII) to (II) sequence to prefer the α bromide followed by phosphateanion displacement via an S$_N$2 process with inversion at the C-1 carbon.

In the scheme leading to formula (III), an acetate moiety is provided at the C-2 carbon to induce trans 1,2-attack at the C-1 carbon due to anchimeric assistance via a dioxolanium ion, i.e., the moiety —O—C$^+$(CH$_3$)—O— between the C-1 and C-2 carbons. Thus, complete removal of the 3 benzyl ethers of (V), e.g., with 10% Pd on carbon at 50 psig of H$_2$ in acetic acid for 3 days, produced triol (VIII) which was phosphorylated selectively on the primary hydroxy group, e.g., with (φO)$_2$POCl in pyridine from 0° to 23° C. for 3 hours, and acetylated, e.g., with acetic anhydride in pyridine for 1 hour, to yield the triacetate (IX) exclusively as the α anomer. The triacetate (IX) was then subjected to the same sequence used for (VII) to (II), with however the change of reacting the bromo compound first with 1.1 mole equivalents of AgBF$_4$ in toluene so as to ionize the bromo compound to generate the dioxolanium ion prior to addition of the phosphate anion. This resulted in a product highly enriched in the α isomer of formula (III), i.e., an 86:14 molar ratio as reported in Example 2b. Failure to do this resulted in a 43:57 α:β mixture of final product, i.e., (III):(II).

The structure of compounds (II) and (III) was examined by $^{13}$C NMR at both 90.55 MHz and 15.1 MHz on a Brucker AM-360 and JEOL FX-60Q spectrometers, respectively, and by $^1$H NMR at 360 MHz on a Brucker spectrometer. $^{13}$C NMR spectra did not show the minor isomer (α or β) present in the enriched products but $^1$H NMR spectra were well suited for quantitation of the minor isomer. The α:β ratios were determined using the resonances for the C-1 hydrogen in the 360 MHz spectra. Further enrichment to provide pure (II) or (III) can be accomplished by ion exchange chromatography, e.g., using DEAE-Sephadex resin, or reverse phase HPLC.

The utility of compounds of the invention of formula (I) as hypoglycemic agents may be determined by measurement of K$_i$ values as competitive inhibitors of rat liver fructose-1,6-biphosphatase and by measurement of half-maximal concentrations as allosteric activators of rat liver 6-phosphofructo-1-kinase, both of these tests being in vitro. An in vivo test for the activity of compounds of the invention is the Epinephrine-Induced Hyperglycemic Model (EIHM). In the EIHM, male Sprague-Dawley rats from Charles River Laboratories, average weight 200–280 grams, maintained on Lab-Blox ® rat chow (Wayne) and provided water ad libitum were used throughout all studies; rats were fasted 18–24 hours prior to treatment with epinephrine (0.2 mg/kg i.p.) which was given intraperitoneally. Drug or vehicle were given 30 minutes prior to epinephrine. Blood samples were taken from the tail vein for measurement of glucose changes prior to and at 45 and 90 minutes after administration of epinephrine bitartrate (Sigma Co., St. Louis, MO). Blood glucose was determined using Autoflo Glucose (Bio-Dyanamics/bmc, Indianapolis, IN).

The following test results were obtained for compound (A) and compounds of the invention:

1. Rat liver fructose-1,6-biphosphatase inhibition*:

| | |
|---|---|
| Compound (A) | K$_i$ = 0.1–0.2 μM |
| Example 1d. (Formula (II)) | K$_i$ = 3.4 μM |
| Example 2b. (Formula (III)) | K$_i$ = 30–40 μM |

*Methodology as described by S. J. Benkovic, et al. in Biochemistry, Vol. 10, No. 26, pp. 4881–4887 (1971).

2. Allosteric activation of rat liver 6-phosphofructo-1-kinase †

| | |
|---|---|
| Compound A | 0.05 μM |
| Example 1d. (Formula (II)) | 1 μM |
| Example 2b. (Formula (III)) | 0.5 μM |

† reported as half-maximal concentrations; methodology as described by S. J. Pilkis, et al. in The Journal of Biol. Chem., Vol. 256, pp. 3171 (1981).

3. EIHM (in vivo)**

| Compound A | 0% at 100 mg/kg i.p. |
|---|---|
| Example 1d. (Formula (II)) | 85% at 100 mg/kg i.p.≠≠ |

** reported as maximum % lowering; methodology as described by G. F. Tutwiler in Biochemical Medicine, Vol. 22, pp. 204 (1979).
≠≠approximately one-half of the drug effect was due to the cyclohexylamine base used to effect crystallization of the drug.

To prepare the pharmaceutical compositions of this invention, one or more compounds of formula (I) of the invention as the active ingredient, is intimately admixed with a pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 250 mg of the active ingredient, e.g, about 25 to 150 mg.

In view of the highly ionic nature of the compounds of formula (I), it may be necessary to administer such compounds in association with a liposome to allow passage across the cell membranes of the patient being treated. The preparation of liposomes as well as the incorporation of active medicaments therein is described by: (1) D. Papahadjopoulos, et al. in Nature, Vol. 252, Nov. 8, 1974, pp. 163–165; (2) D. Papahadjopoulos, et al. in Biochimica et Biophysica Acta, Vol. 363, pp. 404–418 (1974); (3) G. Gregoriadias in The New England Journal of Medicine, Vol. 295, No. 13, Sept. 23, 1976, pp. 704–710; (4) G. Gregoriadias in The New England Journal of Medicine, Vol. 295, No. 14, Sept. 30, 1976, pp. 765–770; (5) M. Finkelstein, et al. in The Journal of Lipid Research, Vol. 19, pp. 289–303 (1978); and (6) D. Papahadjopoulos in Annual Reports in Medicinal Chemistry-14-pp. 250–260, Academic Press, Inc. (1979).

Dosages for compounds of formula (I) of the invention for the treatment of diabetes may be from about 50 to 2000 mg per day for an average human, which dosage may be divided into up to 4 separate administrations.

In the following Examples and throughout the specification, the following abbreviations may be used: psig (pounds per square inch gauge, i.e., uncorrected); MHz (megahertz); $K_i$ (inhibitory equilibrium constant); g (grams); mg (milligrams); α (below the plane of the furan ring); β (above the plane of the furan ring); HOAc (acetic acid); EtOAc (ethyl acetate); THF (tetrahydrofuran); MeOH (methanol); μM (microliters); min (minutes); h (hour(s)); i.p. (intraperitoneally); HPLC (high pressure liquid chromatography); ml (milliliters); mmol (millimoles); M (molar); N (normal); equiv. (molar equivalent); mg/kg (mg per kilogram of body weight); NMR (nuclear magnetic resonance); δ (delta units); s (singlet); br (broad); m (multiplet); $J_{cp}$ (coupling constant); d (doublet); and C, H, N, etc. (the chemical symbols for the elements). All NMR chemical shift data are reported in parts per million (ppm) downfield from tetramethylsilane.

EXAMPLE 1 a.     1-O-Acetyl-2,3,5-O-tris(phenylmethyl)-D-arabinofuranose (V)

A solution of 40 g of commercially available (IV) (Pfanstiehl) was stirred in a 1:1 solution of pyridine/HOAc (100 ml) for 1 h at 100° C. The solvent was evaporated and the product was taken up in ether. The solution was washed twice with $H_2O$ and twice with 1N HCl, then dried ($MgSO_4$), filtered, and concentrated. A near-quantitative yield of (V) was obtained. An analytical sample was purified by chromatography (EtOAc/hexane, 15/85; Waters Prep-500 HPLC), but (V) was typically carried through to the next step without further purification. $^1H$ NMR ($CDCl_3$) δ 7.2 (s, 15H), 6.2 (br s, 1H), 3.6–4.6 (m, 11H), 2.03 (s, αCH_3, 2.1H), 2.00 (s, βCH_3, 0.9H). $^{13}C$ NMR ($CDCl_3$) (δ): 169.9, 138.0 (2C), 137.2, 128.4 (6C), 127.9 (3C), 127.7 (6C), 100.4 (αC-1; 0.7C), 94.3 (βC-1; 0.3C), 69.6–87.1 (7C, m), 21.2 Elemental Analysis:

Calculated for $C_{26}H_{28}O_6$: C, 72.71; H, 6.54. Found: C, 72.52; H, 6.51.

b.     1-O-Acetyl-2,3-O-bis(phenylmethyl)-α-D-arabinofuranose (VI)

To a solution of acetate (V) (20.6 g, 4.46 mmol) in a 1:1 solution of MeOH/HOAc (100 ml) was added 2.0 g of 10% Pd/C and 82 μl of pyridine (0.4%). The solution was shaken on a Parr apparatus under 50 psig of $H_2$. After 24 h the solution was filtered and concentrated, and the residue was purified on a Waters Prep-500 HPLC (EtOAc/hexane, 22/78) to yield 6.4 g of a light yellow oil (39%), homogeneous by TLC. This reaction routinely gave yields of 35–40%. The point at which the reaction is removed from the hydrogenator is determined by when the selectively reduced compound appears greatest by TLC analysis. $^1H$ NMR ($CDCl_3$)δ: 7.3 (s, 10H), 6.2 (br s, 1H), 3.6–4.7 (m, 9H), 2.10 (s, 3H). $^{13}C$ NMR ($CDCl_3$) δ: 169.9, 137.5, 137.1, 128.5 (4C), 128.0 (4C), 127.7 (2C), 100.4 (αC-1), 86.8, 84.6, 82.8, 72.4, 72.1, 62.1, 21.2 Elemental Analysis: Calculated for $C_{21}H_{24}O_6$: C, 67.73; H, 6.50. Found: C, 67.49; H, 6.50.

c.     1-O-Acetyl-2,3-O-bis(phenylmethyl)-α-D-arabinofuranose-5-diphenyl-phosphate (VII)

To a solution of alcohol (VI) (6.0 g, 16.13 mmol) in 50 ml of pyridine at 0° C. under argon was added diphenyl chlorophosphate (3.62 ml, 1.02 equiv). The resulting solution was allowed to warm to 25° C., where it was stirred for 1.5 h. The mixture was diluted with about 100 ml of ether, filtered, washed with $H_2O$ (3×100 ml), dried ($MgSO_4$) and evaporated. The resultant white solid was recrystallized from EtOAc/hexane to give a white powder (86% yield, 8.2 g), mp=62.5°–64.5° C. $^1H$ NMR ($CDCl_3$) (δ) 7.2 (m, 20H), 5.2 (br m, 1H), 3.9–4.7 (br m, 8H), 2.02 (s, 3H). $^{13}C$ NMR ($CDCl_3$) δ: 169.9, 150.3 (2C, d, $J_{CP}$=7.8 Hz), 137.2, 137.0, 129.7

(4C), 128.4 (4C), 127.9 (4C), 127.7 (2C), 125.4 (2C), 120.3 (2C), 120.0 (2C), 100.4 ($\alpha$C-1), 86.5, 83.0, 82.4 (d, $J_{CP}$=8.8 Hz), 72.3, 72.1, 67.6 (d, $J_{CP}$=5.9 Hz), 21.2.

Elemental analysis:

Calculated for $C_{33}H_{33}O_9P$: C, 65.56; H, 5.50; P, 5.12. Found: C, 65.41; H, 5.64; P, 5.20.

d. $\beta$-D-Arabinose-1,5-diphosphate (II)

to a solution of 500 ml of $CH_2Cl_2$ saturated with HBr was added acetate (VII) (5.0 g, 7.53 mmol) at 0° C. After 10 min, the solvent was removed and the residue was evaporated twice from toluene. The resultant gum was dissolved in benzene (50 ml) and added to a mixture of dibenzylphosphate (2.01 g, 1.0 equiv) and triethylamine (1.05 ml, 1 equiv). After 60 min, the solution was filtered and the solvent removed. The residue was diluted with about 5 ml of THF and added to a well-stirred solution of Li metal (about 0.3 g, 6.5 equiv) in a mixture of 200 ml of $NH_3$ and 100 ml of THF at −78° C. The addition of substrate proceeded only as long as the blue color persisted. Then, about 5-mg portions of Li wire were added in alternation with the remaining substrate solution so that the blue color of the reaction was maintained. After addition (about 1.5 h), the solution was stirred for 15 min at −78° C. and crushed ice was added until the blue color dissipated. The solvent was blown off under a stream of nitrogen. The residue was taken up in distilled $H_2O$, filtered through a fine membrane filter (0.45-$\mu$m Nylon-66 by Rainin Instrument Co.), and treated with a pyridinium-Dowex 50X8 resin (from Dowex 50X8 and aqueous pyridine) until the pH was 7. The solution was filtered and a freshly prepared, clear solution of saturated aqueous $Ba(OH)_2$ was added until pH 10. The precipitate was filtered, washed with ethanol, followed by ether, giving 740 mg of a slightly grey powder. The powder was dissolved in a 0.001M solution of pyridine in water using pyridinium-Dowex 50X8 resin. The mixture was filtered and added to about 60 ml of cyclohexylammonium-Dowex 50X8 resin suspended in about 60 ml of a 0.05M solution of cyclohexylamine in water. This mixture was filtered and concentrated. The residue was dissolved in methanol, filtered, and treated with 5 times its volume of ether. The precipitated product was filtered and lyophilized from $H_2O$ to give 640 mg of buff-colored powder (11% yield from (VIII)). $^1$H NMR ($D_2O$) ($\delta$):4.0 (m, 5H), 3.2 (m, 4H), 1.6 (m, 40H), anomeric CH under HOD peak. $^{13}$C NMR:($\delta$) ($D_2O$): 96.5 (C-1, d, $^2J_{CP}$=4.9 Hz), 80.9 (C-4, d, $^3J_{CP}$=6.8 Hz), 76.6 (C-2, d, J=5.9 Hz), 74.5 (C-3, s), 65.5 (C-5, d, $^2J_{CP}$=5 Hz); CHA resonances, 50.1, 30.3, 24.2, 23.7.

Elemental Analysis: Calculated for $C_5H_{17}P_2O_{11}$ 3.4 $C_6H_{13}N.1.4H_2O$: C, 45.36; H, 8.84; N, 7.08; P, 9.21; $H_2O$, 3.75. Found: C, 45.67; H, 8.00; N, 7.14; P, 9.51; $H_2O$, 3.97; Ba, <0.01.

EXAMPLE 2 a. 1,2,3-O-Triacetyl-$\alpha$-D-arabinofuranose-5-diphenylphosphate (IX)

A solution of acetate (V) (26.5 g, 57.4 mmol) was dissolved in 150 ml of HOAc and 6 g of 10% Pd/C was added. After 1.5 days, the solution was filtered and the solvent removed. The residue was evaporated twice from toluene, then dissolved in 70 ml of pyridine and cooled to 0° C. Diphenylchlorophosphate (12.04 ml, 1 equiv) was added. After 2 h at 0° C., 60 ml of acetic anhydride was added and the mixture was heated at 100° C. for 45 min. The major product was isolated using a Waters Prep-500 HPLC (EtOAc/hexane; 3/7) to give 12.8 g of pure, oily (IX) (45% yield). $^1$H NMR ($CDCl_3$) ($\delta$): 7.15 (s, 10H), 6.12 (s, 1H), 5.1 (m, 2H), 4.5 (m, 3H), 2.05 (pair of s, 9H). $^{13}$C NMR ($CDCl_3$) ($\delta$): 169.9, 169.5, 169.0, 150.3 (2C, d, $J_{CP}$=6.8 Hz), 129.7 (4C), 125.4 (2C), 120.2 (2C), 119.9 (2C), 99.3 ($\alpha$C-1), 83.1 (d, $J_{CP}$=7.8 Hz), 80.4, 76.5, 67.1 (d, $J_{CP}$=5.9 Hz), 21.5, 21.0, 20.6.

Elemental Analysis:

Calculated for $C_{23}H_{25}O_{11}P$: C, 54.34; H, 4.96; P, 6.00 Found: C, 54.87; H, 4.98; P, 6.00.

b. $\alpha$-D-Arabinose-1,5-diphosphate (III)

To $CH_2Cl_2$ saturated with HBr (70 ml) was added acetate (IX) (4.5 g, 8.86 mmol) at 0° C. After 10 min, the solution was concentrated and evaporated twice from 10 ml of toluene. The residue was dissolved in toluene (30 ml), cooled to 0° C., and treated with a suspension of $AgBF_4$ (1.9 g, 1.1 equiv) in about 2 ml of toluene. After 10 min, a precipitate formed. The mixture was cooled to −78° C., and a solution of dibenzylphosphate (2.46 g, 1.0 equiv.) and triethylamine (1.23 ml, 1.0 equiv) in 3 ml of toluene was added via syringe. After 10 min, the solution was allowed to warm to room temperature. After a total of 30 min, the solution was filtered, concentrated, dissolved in about 10 ml of THF and added to a blue solution of Li metal (about 0.4 g, 7 equiv) in a mixture of 70 ml of NH/50 ml of THF at −78° C. Small amounts of Li were added in alternation with substrate solution to maintain the blue color. After addition of substrate was complete the solution was kept at −78° C. for 15 min (total time at −78° C. was about 45 min). Distilled $H_2O$ was carefully added to dissipate the blue color. The solvents were removed by a stream of nitrogen overnight. The product was converted to the cyclohexylamine salt as for (II) in Example 1d giving a fine, slightly off-white powder (310 mg, 5.2% yield). $^1$H NMR ($D_2O$) ($\delta$): 4.8–5.2 (m, 1H), 3.6–4.0 (m, 3H), 2.8 (br s, 2H), 0.8–1.8 (m, ca. 30–40H). $^{13}$C NMR ($D_2O$) $\delta$: 102.9 (C-1, d, $^2J_{CP}$=4.0 Hz), 83.7 (C-4, d, $^2J_{CP}$=8.7 Hz), 81.8 (C-2, d, $^2J_{CP}$=7.8 Hz), 76.8 (C-3, s), 64.2 (C-5, d, $^2J_{CP}$=3.0 Hz); CHA resonances, 50.3, 30.4, 24.3, 23.8.

Elemental Analysis: Calculated for $C_5H_{17}P_2O_{11}.3.3C_6H_{13}N$ 1.5 $H_2O$: C, 44.83; H, 8.78; N, 6.96; $H_2O$, 4.07. Found: C, 44.76; H, 8.88; N, 6.68; $H_2O$, 4.14.

What is claimed is:

1. A D-arabinose-1,5-diphosphate salt of the follow formula (I):

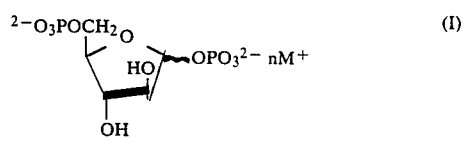

wherein n is about 3 to 4 and M+ is a cation.

2. The salt of claim 1, wherein n is about 3.1 to 3.6.

3. The salt of claim 1, wherein M+ is a cation of an organic base.

4. The salt of claim 3, wherein said organic base is an amine.

5. The salt of claim 4, wherein said amine is ethylamine, diethylamine, triethylamine, pyridine or cyclohexylamine.

6. The salt of claim 1, wherein M+ is an inorganic cation.

7. The salt of claim 6, wherein said inorganic cation is sodium, potassium, lithium or calcium.

8. The salt of claim 1, wherein said salt of formula (I) is of the following formula (II):

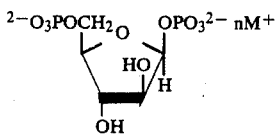
(II)

9. The salt of claim 1, wherein said salt of formula (I) is of the following formula (III):

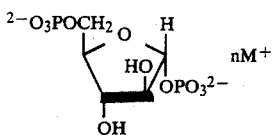
(III)

10. The salt of claim 8, wherein said salt is one formed with cyclohexylamine.

11. The salt of claim 9, wherein said salt is one formed with cyclohexylamine.

12. A D-arabinose-1,5-diphosphate salt isomeric mixture of the following isomers (II) and (III):

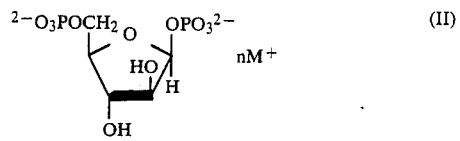
(II)

and

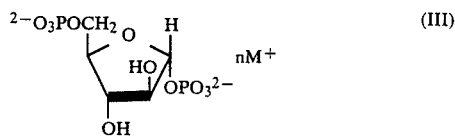
(III)

wherein n is about 3 to 4 and $M^+$ is a cation.

13. The mixture of claim 12, wherein n is about 3.1 to 3.6.

14. A pharmaceutical composition which comprises a salt of claim 1 in association with a pharmaceutically acceptable diluent or carrier.

15. A pharmaceutical composition which comprises a salt of claim 8 in association with a pharmaceutically acceptable diluent or carrier.

16. A pharmaceutical composition which comprises a salt of claim 9 in association with a pharmaceutically acceptable diluent or carrier.

17. A method for treating hyperglycemia in an animal which comprises administering to the animal, the pharmaceutical composition of claim 14.

18. A method for treating hyperglycemia in an animal which comprises administering to the animal, the pharmaceutical composition of claim 15.

19. A method for treating hyperglycemia in an animal which comprises administering to the animal, the pharmaceutical composition of claim 16.

* * * * *